United States Patent
Ganey et al.

(10) Patent No.: US 10,760,058 B2
(45) Date of Patent: *Sep. 1, 2020

(54) ACELLULAR BIOLOGIC COMPOSITION AND METHOD OF MANUFACTURE

(71) Applicant: Vivex Biomedical Inc., Atlanta, GA (US)

(72) Inventors: Timothy Ganey, Tampa, FL (US); Wendy W. Weston, Miami, FL (US); Miguel Quevedo, Miami, FL (US); Stuart Oglesby, Miami, FL (US); Gaetan Jean-Robert Delcroix, Miami, FL (US); Paul C. Schiller, Miami Beach, FL (US); Gianluca D'Ippolito, North Miami Beach, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,475

(22) Filed: May 9, 2017

(65) Prior Publication Data

US 2017/0240862 A1    Aug. 24, 2017

Related U.S. Application Data

(62) Division of application No. 14/682,523, filed on Apr. 9, 2015, now Pat. No. 9,687,511.

(60) Provisional application No. 62/129,351, filed on Mar. 6, 2015, provisional application No. 62/129,337, filed on Mar. 6, 2015.

(51) Int. Cl.
| | |
|---|---|
| *C12N 5/077* | (2010.01) |
| *A61K 35/28* | (2015.01) |
| *A61K 35/32* | (2015.01) |
| *A61L 27/36* | (2006.01) |
| *A61L 27/38* | (2006.01) |
| *A61L 27/44* | (2006.01) |
| *A61L 27/58* | (2006.01) |
| *A61L 27/50* | (2006.01) |
| *A01N 1/02* | (2006.01) |
| *A61L 27/54* | (2006.01) |
| *A61K 35/12* | (2015.01) |

(52) U.S. Cl.
CPC ......... *C12N 5/0669* (2013.01); *A01N 1/0221* (2013.01); *A01N 1/0284* (2013.01); *A61K 35/28* (2013.01); *A61K 35/32* (2013.01); *A61L 27/3604* (2013.01); *A61L 27/365* (2013.01); *A61L 27/3608* (2013.01); *A61L 27/3691* (2013.01); *A61L 27/3834* (2013.01); *A61L 27/446* (2013.01); *A61L 27/50* (2013.01); *A61L 27/54* (2013.01); *A61L 27/58* (2013.01); *A61K 2035/124* (2013.01); *A61K 2300/00* (2013.01); *A61L 2430/00* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,837,539 A | | 11/1998 | Caplan et al. |
| 2002/0132012 A1 | * | 9/2002 | Scarborough ...... A61B 17/7061 424/549 |
| 2005/0013872 A1 | | 1/2005 | Freyman |
| 2007/0191963 A1 | | 8/2007 | Winterbottom et al. |

FOREIGN PATENT DOCUMENTS

WO    2014159662    10/2014

OTHER PUBLICATIONS

Schenke-Layland et al., Ann Thorac Surg 2006; 81: 918-927.*
Thibault et al., Adv Healthc Mater. Jan. 2013; 2(1), pp. 13-24.*
Brockbank et al., Advances in Biopreservation, 2006, pp. 157-196; retrieved from the internet; www.andrew.cmu.edu/user/yr25/TaylorPublications/MJTaylor108.pdf.

* cited by examiner

*Primary Examiner* — Scott Long
*Assistant Examiner* — Evelyn Y Pyla
(74) *Attorney, Agent, or Firm* — David L. King

(57) ABSTRACT

A biological composition has a mixture of mechanically selected allogeneic biologic material derived from bone marrow. The mixture has non-whole cellular components including vesicular components and active and inactive components of biological activity, cell fragments, cellular excretions, cellular derivatives, and extracellular components. The mixture including non-whole cell fractions including one or more of exosomes, transcriptosomes, proteasomes, membrane rafts, lipid rafts. The mixture is compatible with biologic function.

5 Claims, 5 Drawing Sheets

(5 of 5 Drawing Sheet(s) Filed in Color)

ACELLULAR BIOLOGIC COMPOSITION AND METHOD OF MANUFACTURE

RELATED APPLICATIONS

This application is a division of co-pending U.S. application Ser. No. 14/682,523 filed on Apr. 9, 2015 entitled "Acellular Biologic Composition And Method Of Manufacture".

TECHNICAL FIELD

This invention is a tissue regenerative biological composition. More specifically, a composition at least in part formed from bone marrow and a method of manufacture and use of said composition with an acellular mixture.

BACKGROUND OF THE INVENTION

In the area of tissue regeneration or repair, the use of stem cell therapy has been widely touted.

Often, these inventions describe isolating the stem cells, purifying and culturally expanding mesenchymal stem cells. In U.S. Pat. No. 5,837,539, entitled "Monoclonal Antibodies For Human Mesenchymal Stem Cells", Arnold Caplan et al. reported that the cells are preferably culturally expanded, but suggest it is possible to use the stem cells without culture expansion. Caplan also describes a way to isolate stem cells.

A major technological hurdle to producing a safe allogeneic composition with viable cells has been the need to approach a fraction of risk approaching zero by removing all antigenic properties that lead to inflammation factors in a separation to yield only a certain stromal cell type. This has proven both difficult and degrading the quantity of viable cells that can be effectively harvested.

The present invention has yielded a biological composition that is safe and achieves and does so in a method that allows the resultant mixture to be recovered from bone marrow wherein the mixture unexpectedly exhibits evidence of viability independent of mesenchymal cells in the dose and sustains a legacy or memory of the lineages from where the acellular biological composition came which retain the ability to support the emergence of new tissue forms including bone and other tissues.

These and other benefits of the present invention and the method of preparing it are described hereinafter.

SUMMARY OF THE INVENTION

A biological composition has a mixture of mechanically selected allogeneic biologic material derived from bone marrow. The mixture has non-whole cellular components including vesicular components and active and inactive components of biological activity, cell fragments, cellular excretions, cellular derivatives, and extracellular components. The mixture including non-whole cell fractions including one or more of exosomes, transcriptosomes, proteasomes, membrane rafts, lipid rafts. The mixture is compatible with biologic function.

The mixture of mechanically selected material derived from bone marrow. The biological composition preferably has bone particles. The bone particles can be added to the mixture derived from bone marrow. The bone particles include a mixture of cortical bone particles and cancellous bone particles.

The combination of non-whole cell components with a select number of non-whole cell fractions sustains pluripotency in the cells. In a preferred embodiment, the biological composition is predisposed to demonstrate or support elaboration of active volume or spatial geometry consistent in morphology with that of endogenous bone. The biological composition extends regenerative resonance that compliments or mimics tissue complexity. The mixture is treated in a protectant or cryoprotectant prior to preservation or cryopreservation or freeze drying. The composition can be maintained at ambient temperature prior to freeze drying. The protectant or cryoprotectant creates a physical or electrical or chemical gradient or combination thereof for tissue regeneration. The gradient can have a physical characteristic of modulus or topography, such as charge density, field shape or cryo or chemo toxic tendencies. The gradient can have a chemical characteristic of spatially changing compositions of density or species of functional molecules, wherein the molecules can offer a fixed catalytic function as a co-factor. Also, the gradient can have an electrical characteristic of charge based or pH based or electron affinities that confer metastability in biologic potential.

The bone marrow mixture which is derived from a cadaver has separation-enhanced non-whole cell fractions vitality including one or more of the following: separating the fractions from cells heightens their vitality, reversing "arrest" of donors, responsive molecular coupling, matrix quest in neutralizing inflammation or satience by balancing stimulus for repair. The protectant or cryoprotectant is a polyampholyte. The regenerative resonance occurs in the presence or absence of a refractory response. When using a cryoprotectant, the cryopreservation occurs at a temperature that is sub-freezing wherein the cryopreservation temperature is from 0 degrees C. to −200 degrees C. The protection may also be achieved by non-cryogenic means.

The biological composition's non-whole cellular component also can include organelle fragments and the active and inactive components of biological activity which can also include extants of the human metabolome.

A method of making a biological composition of the present invention has the steps of: collecting, recovering and processing bone marrow from a cadaver donor; mechanically separating the cellular or non-cellular components or a combination thereof of bone marrow from cadaverous bone; concentrating by centrifugation and filtering; separation by density gradient centrifugation; collecting non-cellular fractions or non-cellular components or a combination thereof of predetermined density; washing the non-whole cellular fractions or non-cellular components or a combination thereof to create the mixture; quantifying concentrations of non-cellular fractions components at a non-zero entity; suspending to a predetermined concentration in a polyampholyte cryoprotectant; freezing the mixture at a predetermined controlled rate; and packaging a bone blend having particles in the size range of 100 to 300 μm of demineralized cortical bone, mineralized cortical bone and mineralized cancellous bone either within the mixture or separate. These particle size ranges can vary higher or lower depending on the application. At the time of use, the mixture is thawed by immersion in a warm water bath for 2-3 minutes at 37 degrees C. It is diluted in saline without spinning; and then the diluted mixture, with or without the bone blend being intermixed, can be implanted by packing, injection, scaffolding or any other suitable means into a patient.

DEFINITIONS

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

DPBS—Dulbecco's Phosphate Buffered Saline.

CBT-MIXER—Mixing blade for Cancellous Bone Tumbler Jar.

Cold Media—Media used during the preparation of vertebral bodies for initial processing.

Cryopreserved—Tissue frozen with the addition of, or in a solution containing, a cryoprotectant agent such as glycerol, or dimethylsulfoxide, or carboxylated poly-1-lysine.

Freeze Dried/Lyophilized—Tissue dehydrated for storage by conversion of the water content of frozen tissue to a gaseous state under vacuum that extracts moisture.

Normal Saline—0.9% Sodium Chloride Solution.

Packing Media—Media used during initial processing and storage of the processed vertebral bodies prior to bone decellularization.

PBS—Phosphate Buffered Saline.

Processing Media—Media used during bone decellularization that may contain DMEM/Low Glucose no phenol red, Human Serum Albumin, Heparin, Gentamicin and DNAse.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The invention will be described by way of example and with reference to the accompanying drawings in which.

DETAILED DESCRIPTION OF THE INVENTION

With reference to the present invention which is a tissue regenerative biological composition 100 made from bone marrow 200, it is believed best understood by the methods used to process and recover the biological composition, as illustrated in the FIGS. 1-6.

Figure 1:
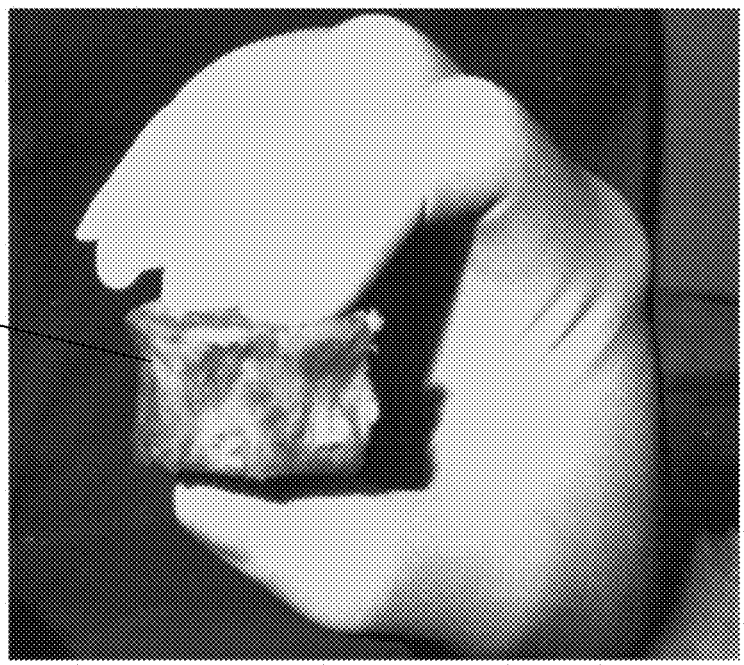
FIG. 1 shows a photograph of a cut vertebral body taken from a spine of a cadaver donor.
Figure 2:
FIG. 2 shows a photograph of the vertebral body after being cut into cubic pieces and immersed in a packing media.
Figure 3:
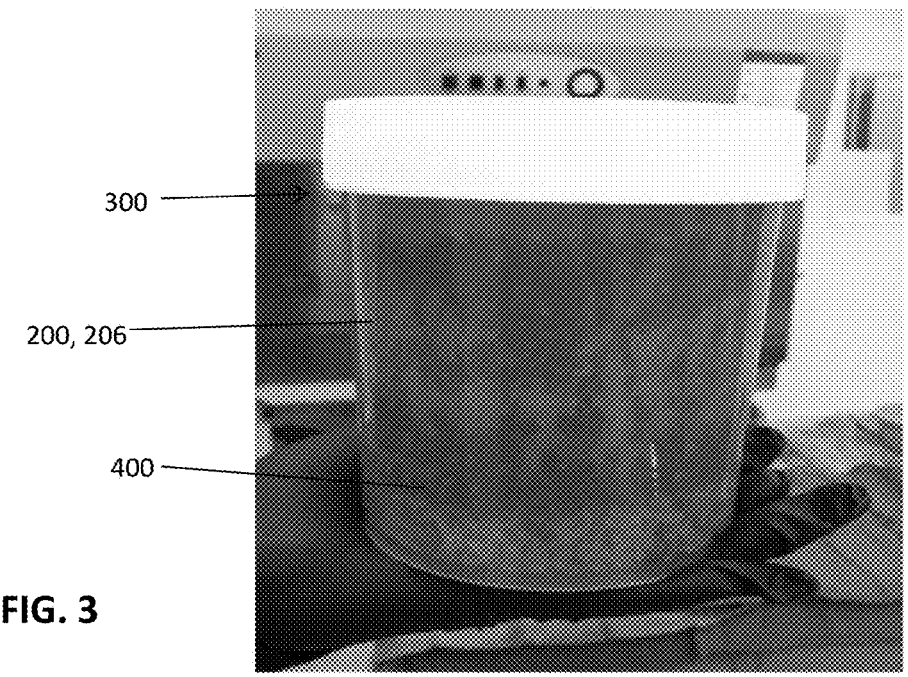
FIG. 3 shows a photograph of the bulk bone material after being ground and immersed in packing media and placed in a jar for later tumbling.
Figure 4:
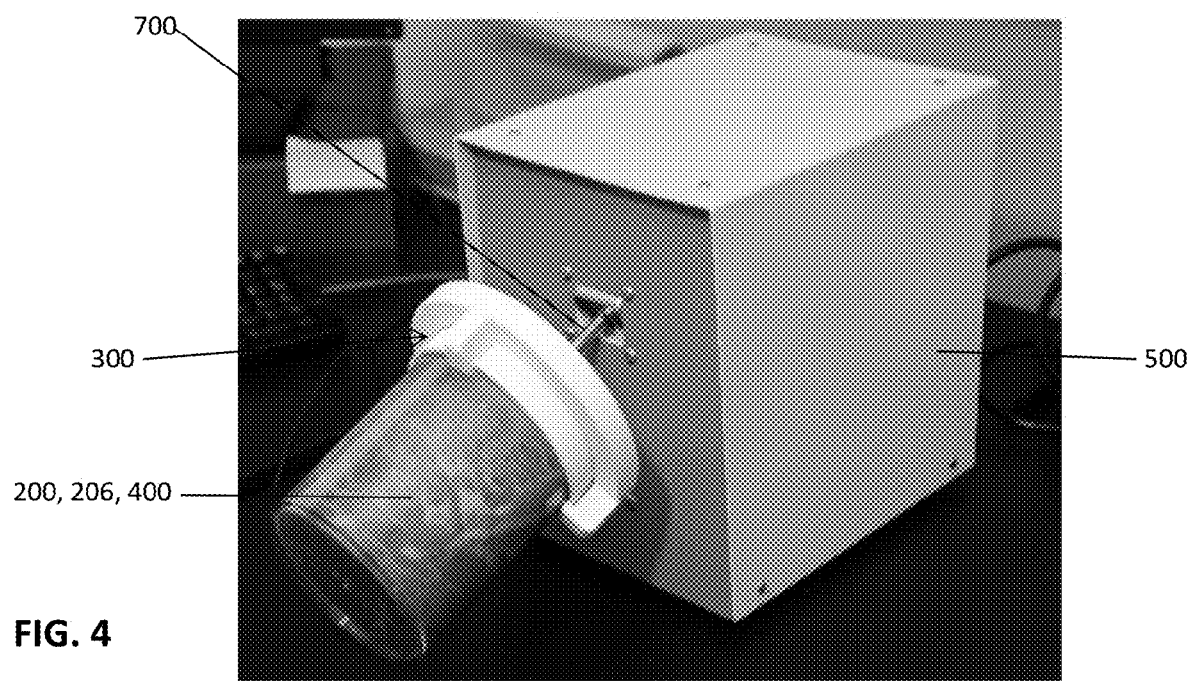
FIG. 4 shows a photograph of the jar with a CBT-Mixer connected to a tumbler.

The first steps are to collect, recover and process bone marrow 200 from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (1 g/L), Sodium Pyruvate; without L-glutamine, or HEPES. This cold media is used for packaging the spine segments for later processing. At this point the spine segment includes a plurality of vertebral bodies 202. The clinical technician must remove as much soft tissue as possible and cut each vertebral body 202 with a saw. These vertebral bodies 202, once cleaned, of all adherent soft tissue around the cortical surfaces will look as shown in FIG. 1.

Once a cleaned vertebral body 202 is obtained, the next step involves cutting each vertebral body 202 into pieces, each piece 204 roughly 1 cm$^3$. The cut pieces 204 being immersed in a packing media 400. The exemplary packing media can be DMEM with 0.5 ml Heparin and 1.25 ml of DNAse added.

Once all the vertebral bodies 202 have been cut, the pieces 204 are taken to the bone grinder. The bone is ground into 4-10 mm pieces using packing media 400 to help the pieces go through the grinder. The ground bone 206 (bulk cortical-cancellous crushed) and all of the packing media 400, estimated volume of 500 ml are transferred into a jar 300 where 0.5-1.0 ml of Gentamicin is added to the jar 300 with ground bone 206 and packing media 400. At this point, the crushed bone 206, including cellular soft marrow 200, is intermixed.

Figure 5:
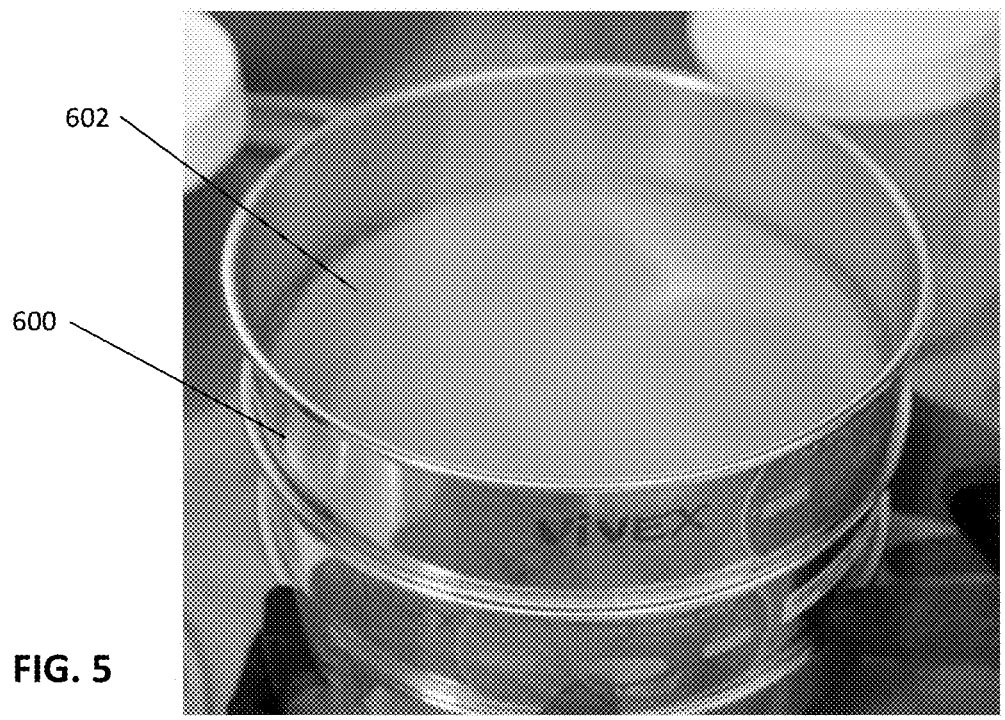
FIG. 5 is a photograph of an exemplary sieve device having sieves sized to separate the solid material.

The step of mechanically separating these cellular components of bone marrow 200 from the cadaverous bone is next performed. Transferring the bulk cortical-cancellous bone chips into a new jar with a CBT-Mixer in the jar. The bulk cortical-cancellous bone chips 206 will go through four cycles as summarized in the table below. Each cycle, after cycle 1, contains three steps using a bone tumbler 500 and sieve set 600. The sieve set 600 has screens 602 of various sizes, for example 500 μm and 180 μm, as shown in FIG. 5.

| Step | Cycle 1 | Cycle 2 | Cycle 3 | Cycle 4 |
|---|---|---|---|---|
| Bone Tumbler | 30 minutes. Using 500 mL Processing Media | 30 minutes Using 500 mL Processing Media | 30 minutes Using 500 mL Processing Media | 30 minutes Using 400 mL Processing Media |
| Sieve Set | Use the 500-μm and the bottom pan sieve. Discard decanted fluid. | Use the 500-μm, 180-μm and bottom pan sieve. Collect decanted fluid. | Use the 500-μm, 180-μm and bottom pan sieve. Collect decanted fluid. | Use the 500-μm, 180-μm and bottom pan sieve. Collect decanted fluid. |
| Centrifuge | N/A | Use decanted fluid. | Use decanted fluid. | Use decanted fluid. |

Figure 7:
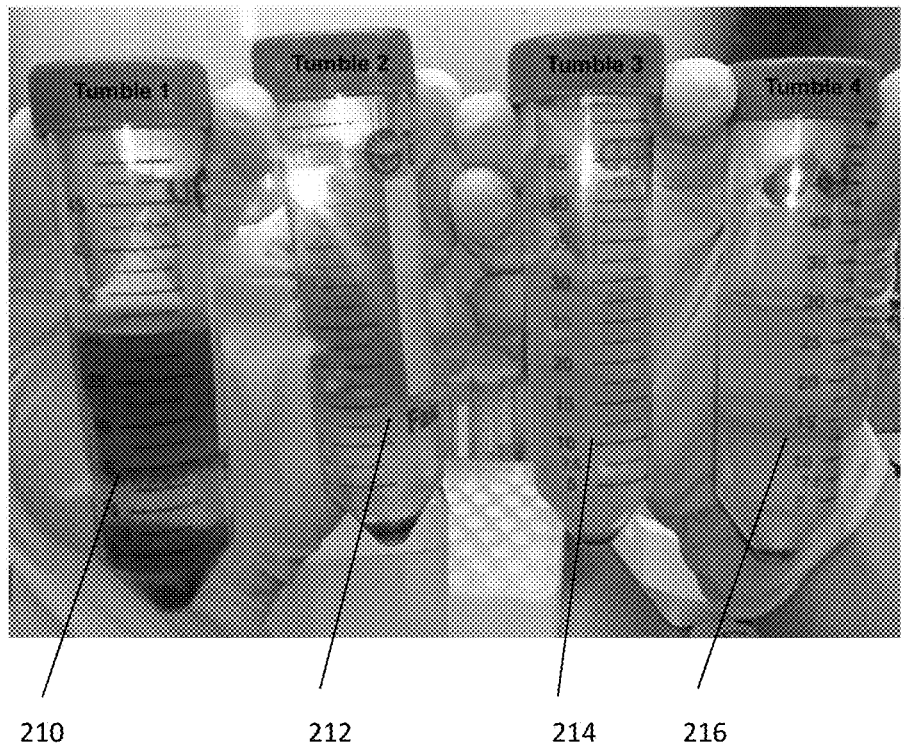
FIG. 7 is a photograph showing the four tumbling steps 1-4 by exemplary collection and Ficoll separation of the decanted fluids, the fluid in tumble 1 being completely discarded to remove unwanted debris.
Figure 8:
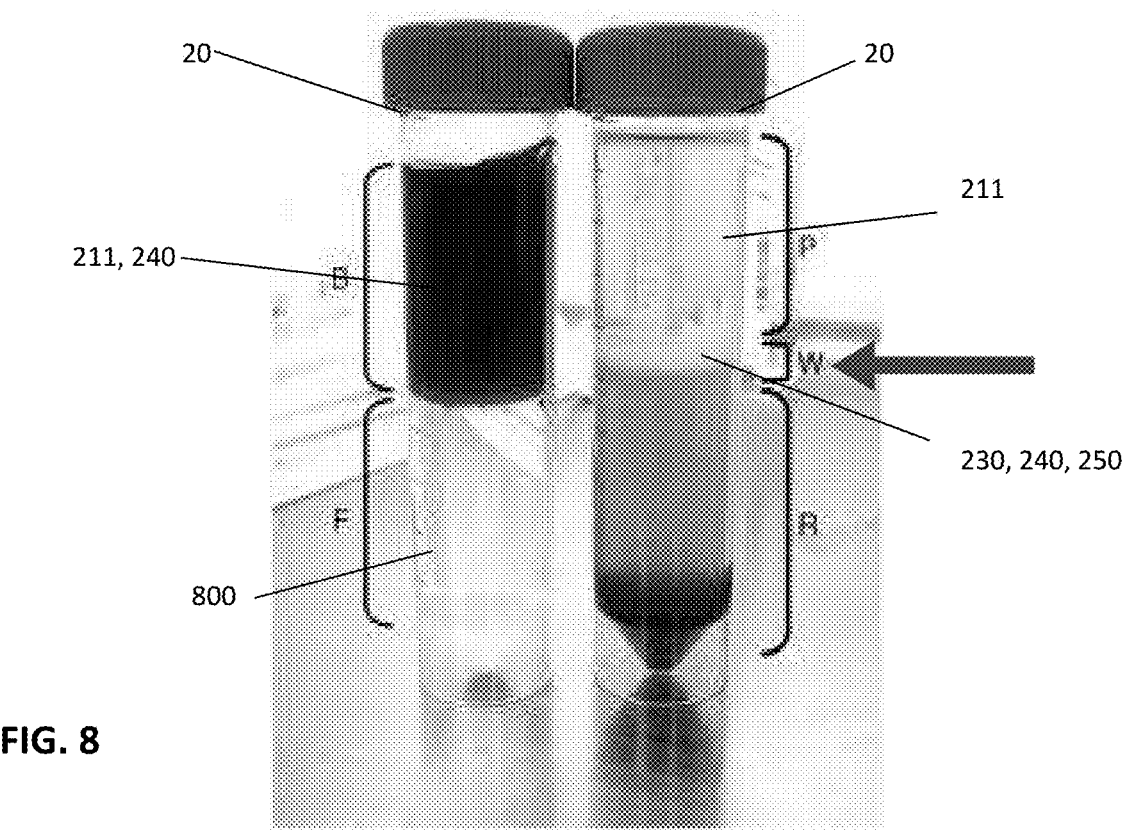
FIG. 8 shows a photograph of two 50 ml vials, the one on the left being prior to centrifuging with a sucrose gradient that is commercially available at the bottom and the material above it. The 50 ml vial on the right is after centrifuging showing the non-whole cell fraction above the interface layer.
Figure 9:
FIG. 9 is a representative photograph of the final packaging.

In cycle 1, the decanted fluid 210 is discarded. To best understand this, an exemplary FIG. 7 shows conical tubes with the decanted fluids after each cycle followed by Ficoll separation. Tumble 1 or Cycle 1 has most of the unwanted cells and debris as evidenced by its dark and red appearance whereas each subsequent cycle 2, 3 and 4 are progressively cleared. This FIG. 7 is only to illustrate the effects of multiple tumbles 1-4 and the value in discarding the decanted liquid 210 after the first tumble 1.

After each subsequent sieving of the bulk bone material 206, the decanted fluid 212, 214, 216 containing the mixture with whole cells is collected and put into a collection jar. When the next three cycles are complete and the decanted fluid is all placed in the collection jar comingling the fluids 212, 214 and 216 to form a decanted fluid 220. Then the centrifugation of the combined decanted fluid 220 occurs by placing the fluid 220 in a number of 250 ml conical tubes using a 100 ml pipette. The centrifuge is programmed to 280×g for 10 minutes at room temperature, preferably about 20 degrees C. The fluid 220 is passed through a blood filter to further remove any bone or spicules or clumps from the suspended cells. This completes the step of centrifuging and filtering. At this point, the mixture including whole cells 240 has been separated from the soft marrow tissue 200 and the remaining cancellous and cortical bone is discarded.

Figure 6:
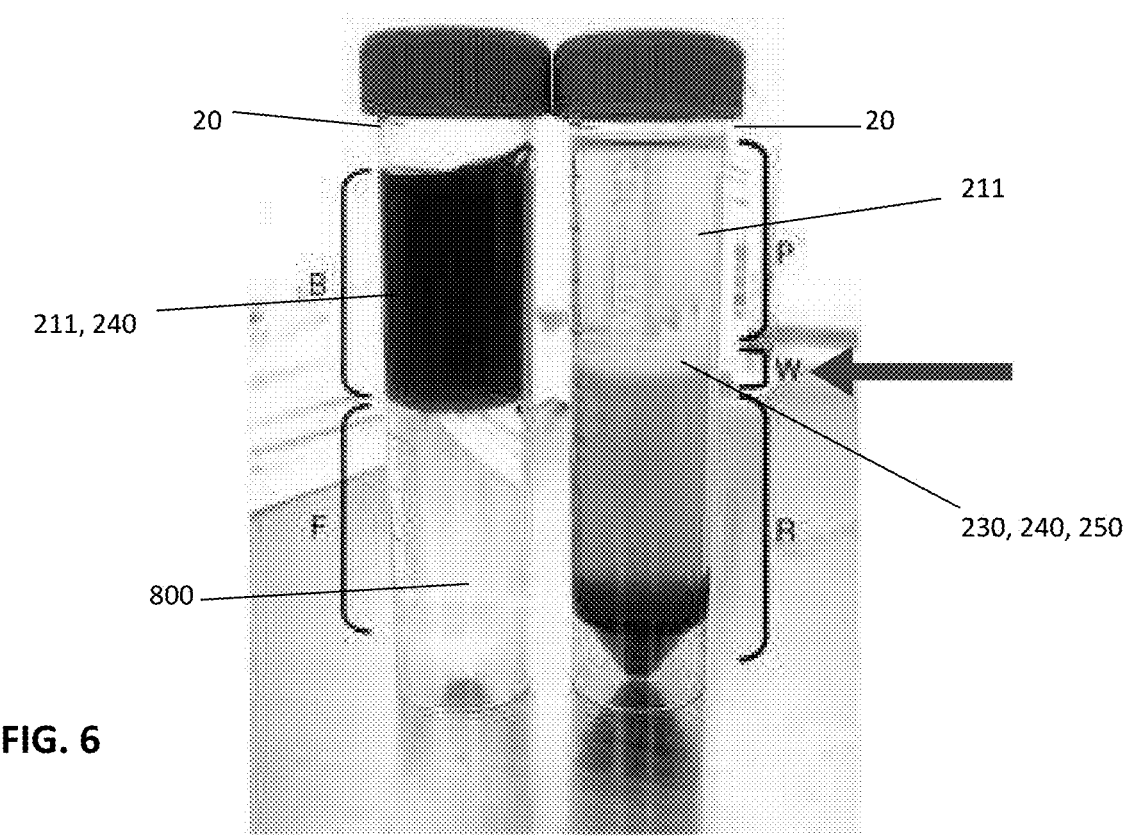
FIG. 6 shows a photograph of two 50 ml vials, the one on the left being prior to centrifuging with the Ficoll that is commercially available at the bottom and the material above it. The 50 ml vial on the right is after centrifuging showing the non-whole cell fraction interface layer.

After this as shown in FIG. 6, the step of separating the non-whole cellular components 211 from the cells 240 from the fluid from the tumble by a density centrifugation occurs. The mixture, including cellular or non-cellular components or a combination thereof, is placed in 50 ml conical tubes 20 with Ficoll 800 and undergoes a Ficoll-Paque separation under centrifugation wherein a cell density gradient is established by spinning a 400×g for 30 minutes at room temperature, preferably about 20 degrees C. The whole cells 240, including whole cells 250, are in the interface 230 and below. The and the non-whole cell components 211 are in the supernatant above the interface. All fluid 211 above the interface is removed and retained which includes the desired non-whole cell components 211 which exclude the whole cells 240, including whole cells 250.

Typically, non-whole cell fragments, or membrane components have a diameter of 40-100 nm and can be separated within a density of 1.13-1.19 g/mL in a sucrose solution, and can be sedimented by centrifugation at 100,000 g. In fact, these fragments, or cell fractions, or microvesicles, have been collectively referred to as exosomes. Ranging in size from 20-1000 nm in diameter, they have been similarly referred to as nanoparticles, microparticles, shedding microvesicles, apoptotic blebs, and human endogenous retroviral particles. There are few firm criteria distinguishing one type of microvesicle from the other.

Following removal of the cell fraction, the supernatant is further filtered through 0.45 and 0.2 μm filters. Exosomes are further collected and separated within the suspension in multiple centrifugation steps with increasing centrifugal strength to sequentially pellet cells (300 g), microvesicles (10,000 g) and ultimately exosomes (100,000 g). Cells are deliberately removed to achieve the non-whole cell fragments and microvesicles.

Subsequent separation using density gradient-based isolation, using sucrose or commercially available prep can be applied to obtain more pure exosome preparations. Recent reports encouraging the use of iodixanol-based gradients for improved separation of exosomes from viruses and small apoptotic bodies are considerations left open to be adopted or adapted in refinement. Differing from sucrose, iodixanol forms iso-osmotic solutions at all densities, thus better preserving the size of the vesicles in the gradient, and both technologies are available to best isolation technology. In addition to these traditional isolation techniques, easy-to-use precipitation solutions, such as ExoQuick™ and Total Exosome Isolation™ (TEI), that have been commercialized reduce the need for expensive equipment or technical know-how. Although their mode-of-action has not been disclosed or validated, these kits are commonly used.

Figure 10:
FIG. 10 is a photograph showing the ground bone.

Once the mixture is completed, the method can include additional steps. This leads to the use of a bone blend 102 shown in FIG. 10, preferably from the same vertebral bone or at least bone from the same donor.

When the mixture is prepared, it can have whole cells or even no whole cells, but will have the mechanically selected non-whole cellular components including vesicular components and active and inactive components of biological activity, cell fragments, cellular excretions, cellular derivatives, and extracellular components.

In one embodiment, the composition includes the whole cells in the mixture. In that embodiment, it is possible to provide bone particles with the mixture either in the mixture or separately to be combined at the time of use.

In one embodiment, the bone is ground to a particle size of 100-300 μm. The bone mixture has 1.5 cc of mineralized cancellous bone 104, 1.5 cc of mineralized cortical bone 105 and 2.0 cc of demineralized cortical bone 106 yielding 30 percent, 30 percent and 40 percent respectively of the total 5 cc (5 gram) of bone material 102. The ranges coincide with the 1 cc of mixture when resuspended in 3 cc of saline to provide a bone particle and mixture for implantation, which can be by packing, injection, scaffolding or any other suitable means, into a patient in a fracture healing procedure, by way of example.

Other ranges of bone particle sized and mixture can be employed depending on the application which, in this example, was bone regeneration. Lower volumes and concentrations may be more suited for less intrusive bone repairs or more if larger if larger amounts of material are needed as in a hip defect or repair.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of preparing a biological composition for use comprises the steps of:

collecting, recovering and processing bone marrow from a cadaver donor;

mechanically separating by spinning or tumbling cellular and non-cellular components of bone marrow from cadaverous bone using a plurality of cycles, wherein the first cycle has a decanted fluid of unwanted cells and debris which is discarded, thereafter subsequent cycles are performed, each subsequent cycle creating a decanted fluid which is retained containing the cellular and non-cellular components, the retained decanted fluid is combined in a collection jar prior to centrifugation and passed through a blood filter to remove any bone or spicules or clumps from the cells and the non-whole cell components;

concentrating the separated cellular and non-cellular components by centrifugation;

separation of cellular and non-cellular components by density gradient centrifugation;

collecting non-cellular fractions or non-cellular components or combinations in a fluid above an interface containing whole cells;

washing the non-cellular fractions or non-cellular components or combinations thereof to create a mixture;

quantifying non-whole cell fraction from the fluid above the interface has a concentration exceeding zero;

suspending the mixture in a polyampholyte cryoprotectant;

freezing the mixture.

2. The method of preparing the biological composition for use of claim 1 further comprises the steps of:

thawing the mixture; and implanting the thawed mixture with a bone blend being intermixed by packing, injection or any other suitable means into a patient.

3. The method of preparing the biological composition for use of claim 2 wherein the step of thawing the mixture occurs at a temperature of 37 degrees C. for 2 to 3 minutes in a warm water bath.

4. The method of preparing the biological composition for use of claim 2 further comprises the step of:

diluting the thawed mixture in saline without spinning.

5. The method of preparing the biological composition for use of claim 3 further comprises the step of:

diluting the thawed mixture in saline without spinning.

* * * * *